(12) United States Patent
Weedon et al.

(10) Patent No.: US 6,258,860 B1
(45) Date of Patent: Jul. 10, 2001

(54) PROCESS FOR THE PRODUCTION OF METHANOL

(76) Inventors: Geoffrey Gerald Weedon, 22D Ridgewood Towers, Diego Martin, Port of Spain (TT); James Bernard Duhan, 30 Eastbourne Terrace, London W2 6LE (GB)

( * ) Notice: Subject to any disclaimer, the term of this patent is extended or adjusted under 35 U.S.C. 154(b) by 0 days.

(21) Appl. No.: 08/860,187

(22) PCT Filed: Jan. 11, 1996

(86) PCT No.: PCT/GB96/00046

§ 371 Date: Jan. 14, 1998

§ 102(e) Date: Jan. 14, 1998

(87) PCT Pub. No.: WO96/21634

PCT Pub. Date: Jul. 18, 1996

(30) Foreign Application Priority Data

Jan. 13, 1995 (GB) .................................................. 9500675

(51) Int. Cl.⁷ ............................ C07C 27/00; C07C 27/26
(52) U.S. Cl. .......................... 518/706; 518/702; 518/703; 518/704; 518/705; 518/713; 518/700; 518/726; 518/706
(58) Field of Search ..................................... 518/702, 703, 518/704, 705, 713, 700, 726, 706

(56) References Cited

U.S. PATENT DOCUMENTS 4,226,795 * 10/1980 Bowman ........................... 210/449.5
5,063,250 * 11/1991 Murayama et al. ................. 518/704

* cited by examiner

*Primary Examiner*—Johann Richter
*Assistant Examiner*—J. Parsa
(74) *Attorney, Agent, or Firm*—Rothwell, Figg, Ernst & Manbeck

(57) ABSTRACT

The invention provides a process for the production of methanol from synthesis gas derived from a carbonaceous feedstock which comprises the following steps: (1) part of the unreacted gas stream from a first methanol synthesis zone is recycled to the first methanol zone; (2) another part of the unreacted gas stream from the first methanol synthesis zone is supplied to a second methanol synthesis zone; (3) part of the unreacted gas stream from the second methanol synthesis zone is recycled to the second methanol synthesis zone; (4) hydrogen is recovered from another part of the unreacted gas from the second methanol synthesis zone to give a hydrogen enriched gas stream and a hydrogen depleted gas stream; and (5) recycling the hydrogen depleted gas stream to the second methanol synthesis zone.

16 Claims, 2 Drawing Sheets

PROCESS FOR THE PRODUCTION OF METHANOL

This application is a 371 of PCT/GB9600046 filed Jan. 11, 1996.

This invention relates to the production of methanol.

Methanol is synthesised in large volumes annually by conversion of a carbonaceous feedstock, more usually a hydrocarbon-containing feedstock, such as natural gas, naphtha, or other oil fraction, into a mixture of carbon oxides and hydrogen. Such a mixture of gases is often referred to as synthesis gas.

The conversion of a hydrocarbon-containing feedstock into synthesis gas can be effected by any appropriate technique, for example by steam reforming, by partial oxidation, by secondary/autothermal reforming, or by a combination of two or more of these processes. Conversion of the carbon oxides and hydrogen to methanol occurs according to the following reactions:

$$CO + 2H_2 \rightleftharpoons CH_3OH$$
$$CO_2 + 3H_2 \rightleftharpoons CH_3OH + H_2O$$

These reactions can be carried out by contacting the synthesis gas with a suitable methanol synthesis catalyst under an elevated synthesis gas pressure, typically in the range of from about 30 bar up to about 100 bar, more usually in the range of from about 50 bar up to about 100 bar, and at an elevated methanol synthesis temperature, typically from about 210° C. to about 270° C. or higher, e.g. up to about 300° C. As an example of a suitable methanol synthesis catalyst there can be mentioned a catalyst comprising a reduced zinc oxide/copper oxide mixture.

In order to obtain maximum usage of carbon oxides and hydrogen it is desirable to ensure that as near a stoichiometric amount of hydrogen is present in the synthesis gas to match the respective contents of the carbon oxides. To this end it may be desirable to add $CO_2$ to the hydrocarbon-containing feedstock or to the synthesis gas, particularly when natural gas is used as feedstock for the production of the synthesis gas, so as to achieve the desired stoichiometry.

A conventional methanol synthesis plant can be considered to comprise three distinct parts, namely:
1. a synthesis gas production section, which produces a mixture of carbon oxides and hydrogen from a hydrocarbon feedstock by a suitable process, such as partial oxidation, secondary/autothermal reforming, or steam reforming, or a combination thereof;
2. a methanol synthesis section, in which crude methanol is produced from the carbon oxides and hydrogen; and
3. a distillation section, in which the final refined methanol product is produced from the crude methanol.

Whilst it is desirable to maximise the efficiency of conversion of hydrocarbon feedstock to methanol, it is generally recognised that the cost of providing process plant and equipment to achieve the highest possible efficiencies within the overall process have hitherto been considered to be economically prohibitive. Hence existing methanol synthesis plant design has generally been a compromise between efficiency and plant investment costs.

In a conventional methanol synthesis plant there are several streams that are considered to be byproduct or waste gas streams from the process. Although these streams contain significant quantities of carbon oxides and hydrogen, and/or methanol, they are conventionally discharged to the plant fuel gas system. Amongst these streams are methanol synthesis loop purge gas, compressor seal gases, flash gases from crude methanol processing, and distillation overhead gases originating from gases dissolved in crude methanol. In addition there may be liquid byproduct streams which also contain significant quantities of methanol. These liquid streams include a heavy byproduct/water stream containing some methanol, often described as fusel oil, and a light byproduct stream, often described as secondary methanol.

These losses of methanol and methanol precursors in the waste streams mean that the synthesis gas production and methanol synthesis sections of the plant must be designed for a higher methanol capacity than necessary for a given refined methanol production rate.

It has hitherto generally been considered uneconomic to recover the potentially valuable constituents from all of these various waste gas and liquid streams, although several schemes have been proposed or implemented to recover such constituents from an individual stream. For example, scrubbing of flash gases or synthesis loop gases with water has been proposed. In addition it has been proposed to obtain additional production of methanol directly from synthesis loop purge gases by passing the purge gases through a purge gas converter containing a second charge of a methanol synthesis catalyst. Another proposal utilises recovery of hydrogen from synthesis loop purge gases with recycle of the recovered hydrogen back to the synthesis loop with additional imported carbon dioxide.

In DE-A-3220995 there is proposed a process for producing methanol from a synthesis gas containing hydrogen and carbon oxides in which the proportion of hydrogen is greater than the stoichiometric proportion required for methanol synthesis and in which unreacted synthesis is partially recirculated in a synthesis loop to the synthesis stage and partly removed as waste gas so that at least a part of the waste gas is returned to the process. In this process the waste gas is separated at least into a CO-rich stream and a residual gas stream and the CO-rich stream is returned to the synthesis gas.

DE-A-3244302 proposes a process for production of methanol in which fresh synthesis gas and recycled synthesis gas recirculated in a loop are taken to a reactor and partially converted to methanol as they flow through a layer of catalyst under methanol synthesis conditions and in which crude methanol is condensed out of the stream leaving the reactor and unreacted synthesis gas is returned in a loop to the reactor inlet. This process is characterised in that an additional methanol synthesis reactor is provided, to which synthesis gas is taken, and which is operated without recirculation, and that synthesis gas which has not reacted in this reactor is taken as fresh synthesis gas to the reactor operated with recirculation of synthesis gas.

Further background to the invention is provided by the following papers:
(a) "The Commercial Proving of the Tube Cooled Converter and its Use as a Purge Gas Reactor" by Simon Early of John Brown—Davy Process Technology, London, United Kingdom presented at 1994 World Methanol Conference, Geneva, Switzerland, Nov. 29–Dec. 1, 1994; and
(b) "Methanol Reactor Design Choices" by P. E. J. Abbott, of ICI Katalco, Billingham, United Kingdom at 1992 World Methanol Conference, Monte-Carlo, Monaco, Dec. 8–10, 1992.

It would be desirable to provide a process for the production of methanol enabling the recovery of significant proportions of the potentially valuable materials normally lost in the gaseous or liquid waste streams from a methanol synthesis plant and their utilisation for the production of further methanol without adding significantly to the cost of producing refined methanol therein.

It would also be desirable to provide a process which would enable the production of methanol from an existing methanol synthesis plant to be significantly increased by addition of a relatively modest amount of additional equipment.

It is accordingly an object of the present invention to provide a process for the production of methanol which enables significant additional methanol production to be achieved economically from an existing methanol synthesis plant, simultaneously with an increased feedstock to methanol conversion efficiency or yield, without requiring modification to existing process equipment items nor increasing the process duties of these items, by the utilisation of byproduct or waste streams from the existing plant.

It is a further object of the present invention to provide an improved methanol synthesis process enabling methanol production to be economically achieved together with an enhanced feedstock utilisation efficiency.

According to the present invention there is provided a process for the production of methanol which comprises:

(A) converting a carbonaceous feedstock in a synthesis gas production plant into a synthesis gas comprising hydrogen and at least one carbon oxide selected from carbon monoxide, carbon dioxide, and mixtures thereof;

(B) providing synthesis gas of step (A) at a methanol synthesis pressure as a compressed synthesis gas;

(C) supplying compressed synthesis gas of step (B) to a first methanol synthesis zone containing a charge of a methanol synthesis catalyst and maintained under methanol synthesis conditions including use of an elevated methanol synthesis temperature and an elevated methanol synthesis pressure;

(D) recovering from the first methanol synthesis zone a first product stream comprising (i) crude methanol and (ii) unreacted gases;

(E) separating the first product stream to form (i) a first crude liquid methanol stream and (ii) a first unreacted gas stream;

(F) recycling by means of a first gas recycle compressor part of the first unreacted gas stream of step (E) to the first methanol synthesis zone;

(G) recovering another part of the first unreacted gas stream of step (E) as a first purge gas stream containing unreacted at least one carbon oxide and hydrogen;

(H) depressurising the first crude liquid methanol stream of step (E) to a refining pressure to produce (i) a degassed first crude liquid methanol stream, and (ii) an off gas;

(I) subjecting the degassed first crude liquid methanol stream of step (H) to at least one refining step in a first methanol refining zone to produce a plurality of streams including (i) a methanol product stream, (ii) a fusel oil stream, (iii) a light byproduct containing secondary methanol stream, and (iv) a methanol-containing vent gas stream;

(J) supplying material of the first purge gas stream of step (G) to a second methanol synthesis zone containing a charge of a methanol synthesis catalyst and maintained under methanol synthesis conditions including use of an elevated methanol synthesis temperature and an elevated methanol synthesis pressure;

(K) recovering from the second methanol synthesis zone of step (J) a second product stream comprising (i) crude methanol and (ii) unreacted gases;

(L) separating the second product stream of step (K) to form (i) a second crude liquid methanol stream and (ii) a second unreacted gas stream;

(M) recycling by means of a second gas recycle compressor part of the second unreacted gas stream of step (L) to the second methanol synthesis zone;

(N) recovering another part of the second unreacted gas stream of step (L) as a second purge gas stream containing unreacted at least one carbon oxide and hydrogen;

(O) subjecting material of the second purge gas stream of step (N) to hydrogen recovery in a hydrogen recovery zone to produce (i) a hydrogen enriched gas stream and (ii) a hydrogen depleted gas stream;

(P) passing a gas containing liquid stream comprising material of the second crude liquid methanol stream of step (L) through a gas recovery zone maintained under gas recovery conditions effective for recovery of dissolved gas present in the gas containing liquid stream;

(Q) recovering from the gas recovery zone of step (P) (i) a substantially methanol free recovered gas stream containing light byproducts and (ii) a second degassed crude liquid methanol stream;

(R) subjecting at least one stream selected from the hydrogen enriched gas stream of step (O) and the recovered gas stream of step (Q) to multistage compression in a multistage gas compression zone comprising a plurality of gas compression stages with an interstage cooler between the or each successive pair of gas compression stages;

(S) recovering from the multistage gas compression zone (i) at least one liquid condensate and (ii) a compressed recovered gas stream; and (T) passing the recovered compressed gas stream of step (S) to the second methanol synthesis zone.

In a particularly preferred process the carbonaceous feedstock comprises natural gas and conversion of the carbonaceous feedstock to synthesis gas in step (A) is effected by a process selected from steam reforming, partial oxidation, secondary/autothermal reforming, and a combination of two or more thereof. Particularly when partial oxidation is used in step (A) for the production of the synthesis gas, the synthesis gas may be produced in step (A) at an elevated synthesis gas production pressure which is high enough to enable methanol synthesis to be effected in step (C) without further compression. However, if the synthesis gas production pressure is lower than the desired methanol synthesis pressure, then the synthesis gas of step (A) can be compressed by means of a synthesis gas compressor to the desired methanol synthesis pressure.

Material of the hydrogen depleted gas stream of step (O) can be used as fuel gas in the synthesis gas production plant. Alternatively material of the hydrogen depleted gas stream of step (O) can be used as supplementary feedstock in the first methanol synthesis zone.

Preferably at least one stream selected from the secondary methanol stream of step (I). the methanol-containing vent gas stream of step (I), and the off gas of step (H) is also supplied to the gas recovery zone of step (P).

Conveniently the gas recovery step (P) includes a water wash step to remove substantially all methanol from the recovered gas stream.

The degassed second crude liquid methanol stream of step (Q) can be sent directly to the first refining zone of step (I) or can be subjected to partial refining in a second methanol refining zone to produce (i) a light byproduct containing purge stream, and (ii) a methanol rich stream. The resulting partially refined methanol rich stream is preferably passed to the first methanol refining zone of step (I).

It is further preferred to subject the fusel oil stream of step (I) to distillation in a fusel oil distillation zone to provide (i) an overhead stream comprising methanol, (ii) a heavy byproduct purge stream, and (iii) a bottom fraction comprising water, and to pass the overhead stream to the first methanol refining zone. At least one stream selected from the heavy byproduct purge stream and the bottom fraction comprising water can be used as supplementary feedstock or fuel in the synthesis gas production plant.

Alternatively the fusel oil stream of step (I) can be subjected to distillation in a fusel oil distillation zone to provide (i) an overhead stream comprising methanol, and (ii) a bottom purge fraction comprising heavy byproducts and water, and for the overhead stream to be passed to the first methanol refining zone. In this case the bottom purge fraction can be used as supplementary feedstock or fuel in the synthesis gas production plant.

It is also contemplated to supply compressor seal gases from the synthesis gas compressor of step (B), when used, to the multistage gas compression zone of step (R). In addition compressor seal gases from at least one of the first and second gas recycle compressors can also be supplied to the multistage gas compression zone of step (R).

Typically the methanol synthesis catalyst is a reduced zinc oxide/copper oxide catalyst. such as ICI 51-3 catalyst. Suitable methanol synthesis conditions include use of a temperature of from about 210° C. to about 300° C., preferably from about 210° C. to about 270° C., and a pressure of from about 30 bar to about 100 bar, preferably from about 50 bar to about 100 bar.

It will thus be appreciated by those skilled in the art that the process of the invention envisages the use of a combination of an additional methanol synthesis system, including a purge gas reactor, together with an additional system for simultaneous recovery of methanol, carbon oxide-containing gases, and hydrogen, and recycle of at least one thereof to this additional methanol synthesis system. The process duties and energy requirements of the first methanol recovery zone are not significantly increased because it is contemplated to provide simultaneous concentration and partial separation of the light and heavy byproducts formed during the methanol synthesis process in the second methanol refining zone and associated equipment.

The process enables maximum additional methanol production to be achieved by simultaneous recovery of methanol and of carbon oxides and hydrogen, from the first methanol synthesis loop purge gas and one or more of the following streams:

compressor seal gases;

flash gases arising from pressure reduction of crude methanol; and distillation column overhead streams containing previously dissolved gases, methanol and methanol byproducts.

In the process of the invention the recovered methanol can be removed simultaneously from one or more of these streams and, in addition, from secondary methanol and fusel oil produced in the first methanol synthesis zone and from crude methanol produced in the second methanol synthesis zone.

Recovery of carbon oxides and hydrogen from one or more of these streams and inclusion of continuous recycle of synthesis gas through the second methanol synthesis zone, or purge gas converter, together with hydrogen recovery facilities to recover hydrogen from the unreacted gas from the second methanol synthesis zone allows maximisation of the overall conversion efficiencies of carbon oxides and hydrogen to methanol.

The extent or the elimination of the continuous recycle of synthesis gas through the second methanol synthesis zone depends upon the stoichiometry of the synthesis gas and level of inert gases and is preferably adjusted so as to optimise the conversion of carbon oxide(s) and hydrogen to methanol.

The methanol produced in the second methanol synthesis zone is refined sufficiently to permit addition thereof to the feed to the first methanol refining zone. This means that the total refined methanol capacity of the first methanol refining zone can be increased without increasing the size of the equipment or increasing its energy consumption or process duties significantly.

Alternatively, if it is not desired to provide a second methanol refining zone and/or fusel oil distillation zone, crude methanol from the gas recovery zone associated with the second methanol synthesis zone can be returned to the first methanol refining zone, provided that it has sufficient capacity, to refine the additional methanol produced in the second methanol synthesis zone.

The process of the invention enables substantial additional production to be achieved from a given amount of hydrocarbon-containing feedstock compared to conventional processes, corresponding to, for example, from about 5% to about 10% of the corresponding capacity of a plant designed according to conventional practice.

In the process of the invention the first and second methanol synthesis zones can be operated at different pressures one from another.

The methanol production process according to the invention permits the plant operator to recover and process more than one of the following byproduct or waste streams:

methanol synthesis loop purge gas;

compressor seal gases;

flash gases arising from pressure reduction of crude methanol;

distillation column overhead streams containing previously dissolved gases, methanol and methanol byproducts;

fusel oil, or heavy byproducts of methanol synthesis, containing methanol; and secondary methanol, or light byproducts of methanol synthesis, containing methanol.

Such recovery and processing enables methanol to be recovered from these streams, as well as carbonaceous material including carbon oxides, which can be recycled.

In the process of the invention there is used in step (P) a gas recovery zone; this can comprise a scrubber which has three primary functions:

to act as a crude methanol liquid/flash gas separator;

to remove methanol from recovered or recycled carbon oxide containing gas streams by contact with water or other suitable solvent; and to remove substantially all dissolved gases from the crude methanol.

In order that the invention may be clearly understood and readily carried into effect, a methanol synthesis plant designed to operate a preferred process in accordance with the invention will now be described, by way of example only, with reference to the accompanying drawings, in which:

It will be understood by those skilled in the art that the drawings illustrate a single type of plant for operating the process of the invention. Moreover it will be appreciated that, since the drawings are diagrammatic, further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

Figure 1:
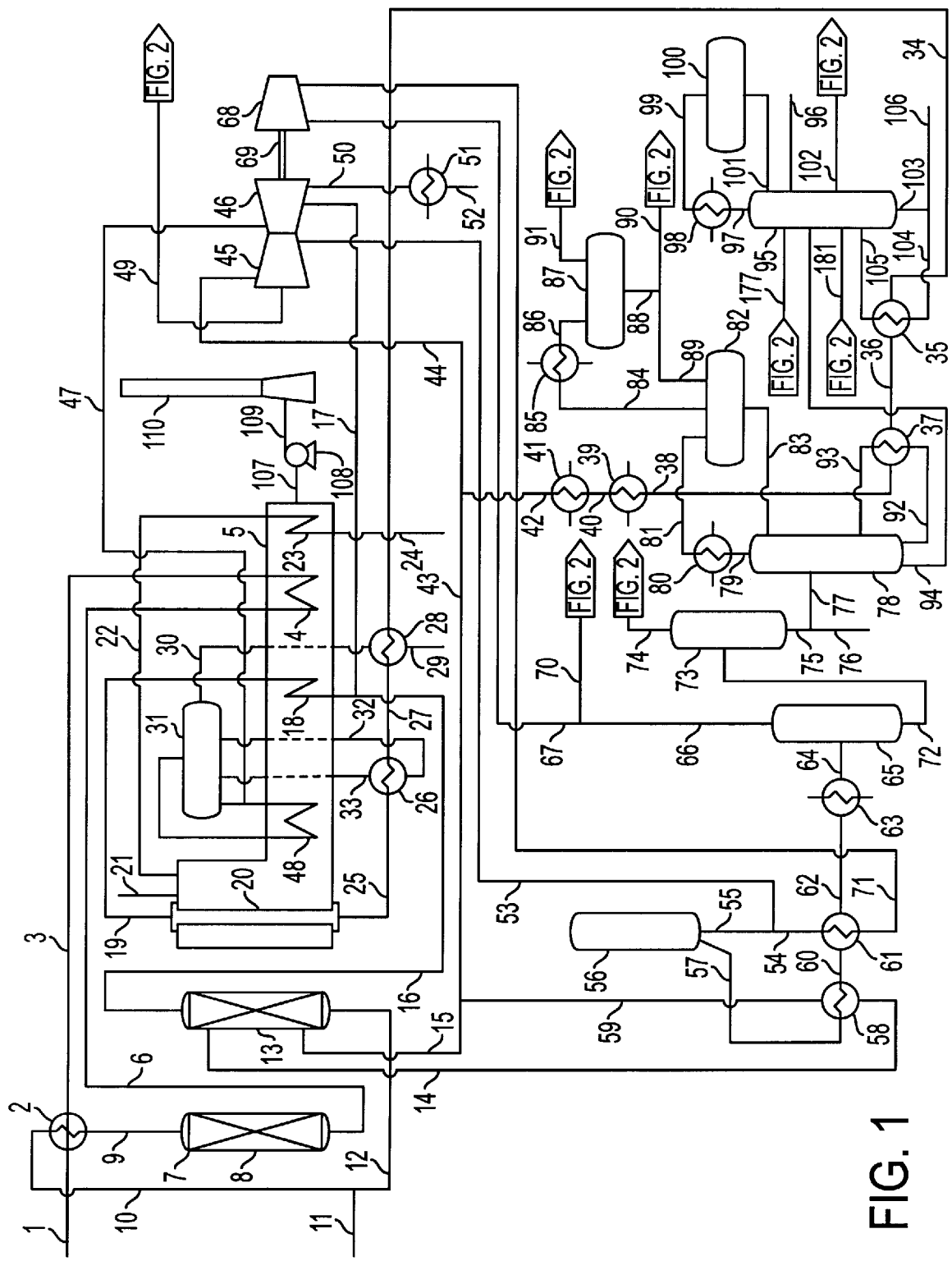
FIG. 1 is a flow diagram of a part of the methanol synthesis plant.

Referring to FIG. 1 of the drawings, a stream of natural gas is supplied to the plant in line 1 at a pressure of approximately 30 bar, is heated in passage through heat exchanger 2, and passes on in line 3 to desulphurisation preheater 4 which is mounted in the flue gas duct of steam reformer furnace 5. The natural gas feed typically contains a minor amount of sulphur as hydrogen sulphide which is a poison to downstream catalysts. The heated natural gas in line 6, which is now at a temperature of approximately 380° C., passes on to desulphurisation reactor 7 which contains a charge 8 of desulphurisation catalyst. Suitable desulphurisation catalysts include nickel molybdate and zinc oxide.

The desulphurised gas flows on in line 9, through heat exchanger 2 into line 10 and is optionally mixed with carbon dioxide from line 11. The resulting mixture flows on in line 12 to saturator 13 in which the gas flows countercurrent to hot water from line 14. A water stream is recovered from the bottom of saturator 13 in line 15.

In passage through saturator 13 the gas mixture is heated and saturated with water vapour. The water-saturated gas mixture exits the saturator at about 200° C. in line 16 and contains approximately 60% of the steam required for subsequent reforming. The gas/steam mixture in line 16 is mixed with further steam from line 17 and passes on through mixed feed heater 18, which is mounted in the flue gas duct of reformer furnace 5. In heater 18 the temperature of the gas/steam mixture is raised to about 560° C. The resulting hot gas in line 19 is fed to the inlet end of steam reformer tubes 20. Although only a single steam reformer tube 20 has been illustrated in FIG. 1 for the sake of clarity, it will be appreciated that there would in practice be a multiplicity of steam reformer tubes 20 each containing a charge of a suitable steam reforming catalyst, for example a supported nickel catalyst. Steam reformer tubes 20 are heated by means of burners which are, for example, arranged in rows between the reforming tubes 20. Fuel, for example natural gas, a waste gas, or a mixture thereof, is supplied to the burners in line 21. Hot air for combustion is supplied by means of line 22; this hot air is heated by passage of air through combustion air preheater 23, which is also mounted in the flue gas duct of reformer furnace 5, from air inlet 24.

In the reformer tubes 20, the feed mixture of natural gas, steam, and possibly also added $CO_2$, is reformed to a mixture of carbon monoxide, carbon dioxide, hydrogen and methane, a mixture commonly known as synthesis gas. The synthesis gas leaves the reformer tubes at 880° C. and 20 bar in line 25.

In the presence of the nickel catalyst at elevated temperatures, steam reacts with gaseous hydrocarbons at elevated temperatures and pressures to give a synthesis gas consisting of carbon dioxide, carbon monoxide, and hydrogen, together with methane and possibly other inert gases. The concentration of each constituent in the synthesis gas depends on the ratio of steam to hydrocarbon passing over the catalyst, and on the temperature and pressure at which the gases leave the catalyst. The reactions taking place are complex but the end product is determined by two reactions, i.e.

(i) the water gas shift equilibrium reaction:

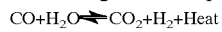

(ii) the steam-methane equilibrium reaction

Overall the reactions are endothermic. A large excess of steam and a high temperature are required to move the equilibrium to the right and to reduce the residual methane content of the synthesis gas.

In operation sufficient $CO_2$ is preferably introduced through line 11 to provide a stoichiometric synthesis gas in line 25; hence the rate of $CO_2$ addition is preferably controlled so that, on a molar basis, the hydrogen content is equal to twice the carbon monoxide content plus three times the carbon dioxide content.

The hot synthesis gas at a temperature of 880° C. enters reformed gas boiler 26 where it is cooled by raising high pressure steam. From here the gas proceeds via line 27 to a high pressure boiler feed water heater 28 where it is further cooled by preheating boiler feed water supplied in line 29. The resulting heated boiler feed water passes on in line 30 to high pressure steam drum 31. Water to raise high pressure steam is passed from drum 31 through line 32 to reformed gas boiler 26, the resulting high pressure steam being fed back to the drum 31 in line 33.

The synthesis gas flows on from boiler feed water heater 28 in line 34 and is further cooled by passage through a reboiler 35. The two phase mixture leaving this unit is separated into gas and aqueous liquid streams in a knock-out drum (not shown), the gas being sent forward in line 36 to a further reboiler 37. Again a two phase mixture is recovered and separated by passage through a further knock-out drum (not shown). The gas flows on in line 38 to a demineralised water heater 39. Any condensate is removed in a further knock-out drum (which is not shown), the gas passing on in line 40 to cooler 41 which is supplied with water. The two phase mixture in line 42 is separated in a knock-out drum (not shown) from which the condensate is passed in line 43 for admixture with the water in line 15. The gas flows on in line 44 to compressor 45. This is driven by steam turbine 46 which is supplied in line 47 with high pressure steam from drum 31 which has been further heated by passage through superheater 48 mounted in the flue gas duct of reformer furnace 5. Reference numeral 49 indicates a line by means of which compressor seal gases are recovered for further treatment as will be described below.

Medium pressure steam is recovered from the low pressure side of compressor 46 in line 17. Low pressure steam is recovered from the exit end of turbine 46 and is passed in line 50 to condenser 51, the resulting condensate being removed from the plant in line 52.

Although synthesis gas compressor 45 is illustrated in FIG. 1 as a single stage compressor, it may be desirable to use a two stage compressor with an intercooler for cooling the synthesis gas. Any condensate formed is in this case removed by means of an interstage knockout drum downstream from the intercooler.

Compressed gas is fed from compressor 45 in line 53, is admixed with recycle gas from line 54 and then passes by way of line 55 to methanol converter 56.

In the illustrated methanol converter 56 the entering gas is preheated to reaction temperature by upward passage through tubes mounted in the hot catalyst bed. On reaching the top of these tubes it flows out and down the outside of the tubes into the catalyst bed where methanol synthesis occurs. The heat of reaction is used to preheat the incoming feed gas which moderates catalyst temperatures.

Typical methanol synthesis conditions include use of a pressure in the region of 80 bar and an outlet temperature of from about 240° C. to about 270° C. using a copper/zinc catalyst, for example the catalyst sold as ICI 51-3.

The methanol synthesis equilibria are as follows:

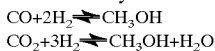

$$CO + 2H_2 \rightleftharpoons CH_3OH$$
$$CO_2 + 3H_2 \rightleftharpoons CH_3OH + H_2O$$

It will be appreciated that an ideal synthesis gas should have a hydrogen content equal to twice the carbon monoxide content plus three times its carbon dioxide content.

Typically, the gas in line 55 contains about 10 to about 20 vol % carbon oxides, the balance being hydrogen, methane and nitrogen.

Hot gas exits methanol converter 56 in line 57 to saturator water heater 58 which is fed with the stream in line 59 obtained by mixing the streams from lines 15 and 43. The resulting heated water stream in line 14 is fed to saturator 13 as described above.

The cooled reaction product stream flows on in line 60 to loop interchanger 61 in which it is cooled against recycle gas. A small amount of condensation takes place in loop interchanger 61.

The mixed phase stream passes on from loop interchanger 61 in line 62 to an air cooler (not shown) which acts as a crude methanol condenser, and then on to crude methanol trim condenser 63 which is water cooled. The two phase mixture passes in line 64 to a crude methanol separator 65 where the crude methanol is separated from the uncondensed gases and from which the uncondensed "circulation" gases are returned in lines 66 and 67 to the suction side of circulator 68 which is conveniently coupled to the shaft 69 of turbine 46. Alternatively circulator 68 is driven by a separate turbine.

Reference numeral 70 represents the main plant methanol synthesis loop purge gas line. This purge gas stream is necessary in order to maintain the level of inerts (methane or nitrogen) and excess hydrogen in the reactor 56 near the optimum conditions. The purge gas stream in line 70 is treated further in the part of the plant shown in FIG. 2, as described below.

Reverting to FIG. 1. the gas in line 71 passes through loop intercooler 61 to line 54.

The crude methanol from crude methanol separator 65 is fed by way of line 72 through a letdown valve (not shown) to a pressure of about 6 bar and is then admitted to a crude methanol letdown vessel 73. Gases dissolved in the crude methanol flash off and are separated from the liquid in the crude methanol letdown vessel 73 before being recovered for further treatment (as described below) in line 74.

Liquid crude methanol flows on in line 75 from the bottom of vessel 73 and is mixed with water supplied from line 76 to provide a water concentration in the liquid in line 77 of between about 20% by weight and about 25% by weight. This liquid is fed to topping column 78 from which a "lights" stream comprising remaining traces of any gases dissolved in the stream in line 77 and dimethyl ether is recovered overhead in line 79. This overhead stream is passed through topping column primary condenser 80 in which the bulk of the condensibles liquefy. The resulting liquid is fed via line 81 at a temperature of approximately 68° C. into reflux drum 82 from which a reflux stream passes back into topping column 78 via line 83. The vapour stream from condenser 80 is passed through line 84 to secondary condenser 85 which cools it to approximately 40° C. The resulting two phase mixture flows on in line 86 to drum 87 from which secondary methanol is returned to reflux drum 82 through lines 88 and 89. A secondary methanol purge stream is recovered in line 90. Reference numeral 91 indicates a vent from drum 87, the gas stream in which is treated further in the part of the plant shown in FIG. 2.

A stream is withdrawn from the bottom of topping column 78 in line 92 and is passed through reboiler 37 before being returned to the column in line 93.

A topped methanol stream is fed by way of line 94 to refining column 95. The final product is recovered as a liquid from a tray in the top part of refining column 95 in line 96, while a vaporous overhead stream in line 97 is condensed in condenser 98, the condensate from which passes in line 99 to drum 100. A reflux stream returns to column 95 in line 101.

A stream of fusel oil is recovered in line 102. A water stream is recovered from the bottom of refining column 95 in line 103 and is recycled in line 104 to reboiler 35 and then returned to the column in line 105. Part of the water stream in line 103 is discharged in line 106 for effluent treatment.

Flue gas from reformer furnace 5 is drawn through duct 107 by blower fan 108 which effects discharge thereof to the atmosphere by way of duct 109 and stack 110.

Figure 2:
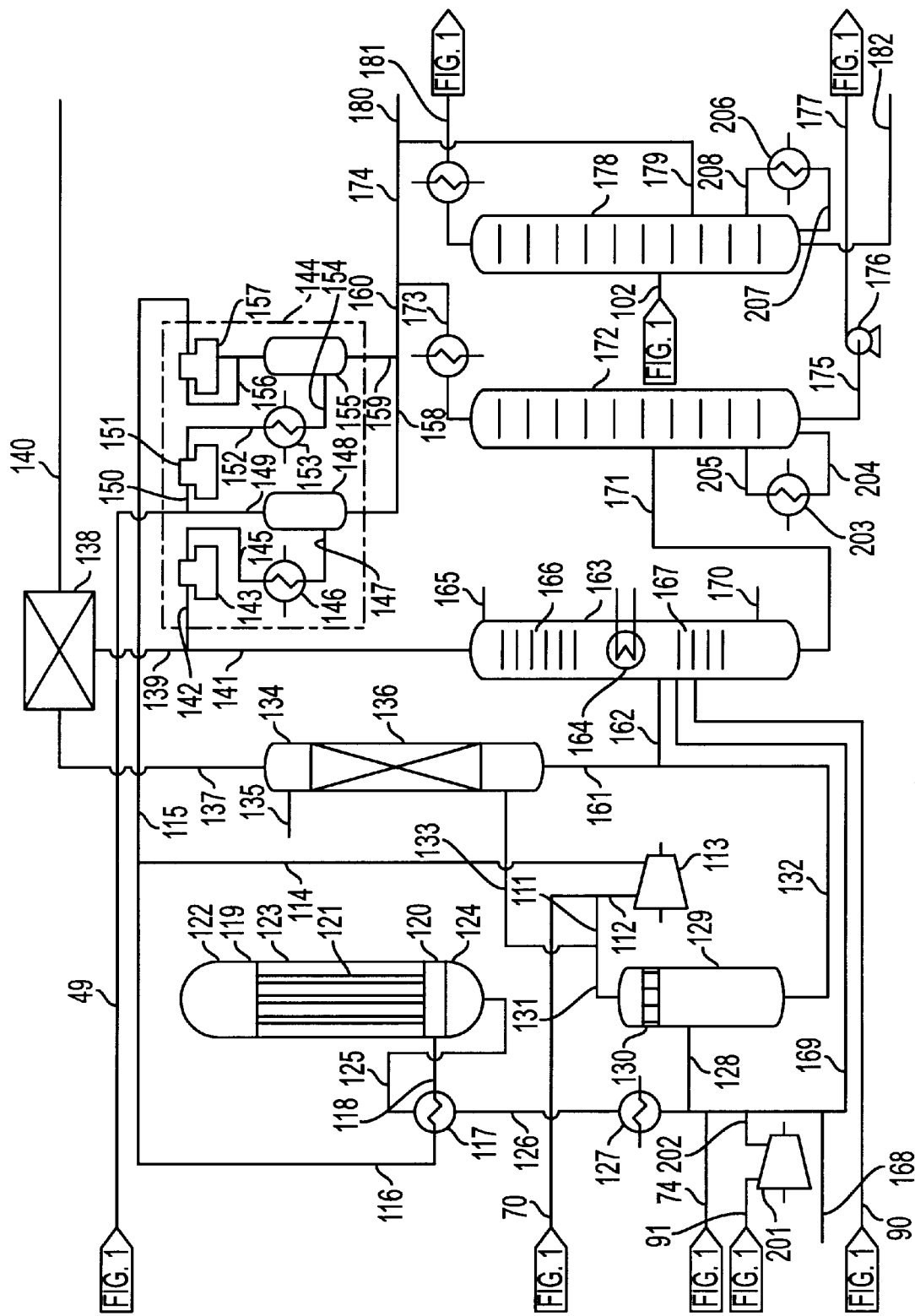
FIG. 2 is a flow diagram of the remainder of the plant.

As shown in FIG. 2, the purge gas stream in line 70 is combined with a gas recycle stream from line 111. The resulting mixed gas stream in line 112 is compressed by means of compressor 113 to pass on in line 114. The stream in line 114 is then mixed with other recovered gases from line 115; the resulting gas stream in line 116 is preheated in heat interchanger 117 before passing through line 118 to a purge gas reactor 119 which can be of the same general design as methanol converter 56. Hence gas from line 118 enters header 120, passes upwards through tubes 121, only three of which are shown in FIG. 2 for the sake of clarity, enters headspace 122 and then passes downward through the catalyst bed 123 to emerge from the bottom thereof to flow around header 120 into bottom space 124. The methanol containing stream exits purge gas reactor 119 in line 125 and passes through heat interchanger 117 into line 126. The gas is then cooled further by means of cooler 127. Cooler 127 cools the product stream to less than 80° C. to condense the majority of the methanol contained in the reaction product stream from the purge gas reactor 119. The resulting mixture of gas and liquid flows by way of line 128 into separator 129, which is fitted with a liquid entrainment prevention device 130, such as a demister pad, to prevent carry over of liquid into the recovered gas stream 131. Liquid methanol product is recovered from the bottom of separator 129 in line 132.

The liquid-free gas stream in line 131 is split into two streams, one being the stream in line 111 and the other stream in line 133 flowing on to scrubber 134. This is supplied from line 135 with water which flows down scrubber 134 over packing 136 to remove methanol from the upflowing gas. The resulting methanol-free gas stream passes on in line 137 to a hydrogen separation unit 138. This can operate using any convenient known technique, for example pressure swing absorption, membrane technology, liquefaction, or a combination of two or more thereof. The use of membrane technology is preferred, often being the most economical.

A hydrogen-enriched gas stream is recovered from hydrogen separation unit 138 in line 139 while a hydrogen-depleted gas stream is passed as off gas to line 140. The off gas in line 140 can be fed to the burners of the steam reformer furnace 5 by way of line 21. Alternatively it can be combined with the natural gas feed in line 1 or with the carbon dioxide stream in line 11.

The recovered hydrogen in line 139 contains small amounts of other gases, predominantly carbon dioxide, and is mixed with other recovered gases from line 141. The combined stream in line 142 is then compressed by the first stage 143 of a multistage compressor 144. The compressed gas stream in line 145 passes through interstage cooler 146 from which the resulting mixture of gas and condensate flows in line 147 to interstage separator 148. The gaseous components from interstage separator 148 flow on in line 149 and are admixed with the compressor seal gas stream 49. The resulting mixed gas stream in line 150 is further compressed by the second stage compressor 151 of the multistage compressor 144. The gas stream in line 152 is cooled in a further interstage cooler 153 and the resulting gas mixture passes on in line 154 to a further separator 155. The recovered gaseous components from separator 155 pass on in line 156 to the final stage 157 of the multistage compressor 144 to provide the stream in line 115. The liquid streams from separators 148 and 155 are recovered in lines 158 and 159 respectively and are combined to form a stream in line 160.

The methanol-containing stream in line 132 is combined with the aqueous methanol-containing stream in line 161 from the bottom of scrubber 136. The mixed stream that results flows on in line 162 to a further scrubber 163 which contains a condenser 164. Uncondensed gases pass upward in scrubber 163 against a downflowing stream of water from line 165 which flows down through trays or packing 166. Scrubbed gas is passed on in line 141 to multistage compressor 144, as described above. Any light by-products, such as dimethyl ether, are recovered in liquid form in line 160. The stream in line 141 contains carbon oxides and most of those methanol synthesis by-products which are more volatile than methanol which have been produced in methanol reactor 119.

The secondary methanol stream in line 90 is also fed to a lower part of scrubber 163 which contains trays or packing 167. The stream in line 91 is compressed by means of compressor 201 and the resulting compressed gas stream in line 202 is combined with the stream in line 74 and fed to scrubber 163, optionally in admixture with additional $CO_2$ from line 168, by way of line 169. Reference numeral 170 indicates a line for supply of steam to the bottom of scrubber 163.

A liquid stream containing methanol, water and minor amounts of impurities is recovered from the bottom of scrubber 163 in line 171 and is fed to a lights column 172. "Lights", chiefly consisting of light byproducts pass overhead in line 173 and are admixed with the material from line 160 to form a stream in line 174. A topped crude methanol stream is taken from the bottom of lights column 172 in line 175 and is pumped by pump 176 to line 177 for return to refining column 95 (see FIG. 1). Reference numeral 203 indicates a reboiler for lights column 172 to which a bottoms stream in line 204 is passed, while line 205 is the recycle line from reboiler 203 to lights column 172.

The fusel oil stream 102 from column 95 (see FIG. 1) is passed to an additional "heavies" refining column 178 (see FIG. 2) in which concentration of products less volatile than methanol, such as higher alcohols and paraffins occurs; these less volatile products are discharged via line 179 and are admixed with the stream from line 174. The resulting stream in line 180 is recycled to the synthesis gas production facility of FIG. 1 as supplementary feedstock. The overhead stream from "heavies" refining column 178 in line 181 contains mostly methanol; it too is supplied to column 95 (see FIG. 1). The bottoms fraction from column 178 comprises mainly water and is recovered in line 182 and is either discharged from the plant or recycled to the synthesis gas section. Reference numeral 206 indicates a reboiler for "heavies" refining column 178 to which a bottoms stream in line 207 is passed, while line 208 is the recycle line from reboiler 206 to "heavies" refining column 178.

By providing "heavies" refining column 178 a greater than usual draw of fusel oil can be taken in line 102. This allows more crude methanol than normal to be processed in the refining section comprising columns 78 and 95 without requiring the expenditure of significant additional energy to effect refining of the additional methanol produced.

In a modification of the plant of FIGS. 1 and 2 line 179 is omitted so that the bottoms fraction in line 182 contains also the products less volatile than methanol, such as higher alcohols and paraffins. This bottoms fraction can be used, for example, in the synthesis gas production plant as part of the feedstock or as fuel.

What is claimed is:

1. A process for the production of methanol which comprises:

(A) converting a carbonaceous feedstock in a synthesis gas production plant into a synthesis gas comprising hydrogen and at least one carbon oxide selected from carbon monoxide, carbon dioxide, and mixtures thereof;

(B) providing synthesis gas of step (A) at a methanol synthesis pressure as a compressed synthesis gas;

(C) supplying compressed synthesis gas of step (B) to a first methanol synthesis zone containing a charge of a methanol synthesis catalyst and maintained under methanol synthesis conditions including use of an elevated methanol synthesis temperature and an elevated methanol synthesis pressure;

(D) recovering from the first methanol synthesis zone a first product stream comprising (i) crude methanol and (ii) unreacted gases;

(E) separating the first product stream to form (i) a first crude liquid methanol stream and (ii) a first unreacted gas stream;

(F) recycling by means of a first gas recycle compressor part of the first unreacted gas stream of step (E) to the first methanol synthesis zone;

(G) recovering another part of the first unreacted gas stream of step (E) as a first purge gas stream containing unreacted at least one carbon oxide and hydrogen;

(H) depressurizing the first crude liquid methanol stream of step (E) to a refining pressure to produce (i) a degassed first crude liquid methanol stream, and (ii) an off gas;

(I) subjecting the degassed first crude liquid methanol stream of step (H) to at least one refining step in a first methanol refining zone to produce a plurality of streams including (i) a methanol product stream, (ii) a fusel oil stream, (iii) a light byproduct containing secondary methanol streamy and (iv) a methanol-containing vent gas stream;

(J) supplying material of the first purge gas stream of step (G) to a second methanol synthesis zone containing a charge of a methanol synthesis catalyst and maintained under methanol synthesis conditions including use of an elevated methanol synthesis temperature and an elevated methanol synthesis pressure;

(K) recovering from the second methanol synthesis zone of step (J) a second product stream comprising (i) crude methanol and (ii) unreacted gases;

(L) separating the second product stream of step (K) to form (i) a second crude liquid methanol stream and (ii) a second unreacted gas stream;

(M) recycling by means of a second gas recycle compressor part of the second unreacted gas stream of step (L) to the second methanol synthesis zone;

(N) recovering another part of the second unreacted gas stream of step (L) as a second purge gas stream containing unreacted at least one carbon oxide and hydrogen;

(O) subjecting material of the second purge gas stream of step (N) to hydrogen recovery in a hydrogen recovery zone to produce (i) a hydrogen enriched gas stream and (ii) a hydrogen depleted gas stream;

(P) passing a gas containing liquid stream comprising material of the second crude liquid methanol stream of step (L) through a gas recovery zone maintained under gas recovery conditions effective for recovery of dissolved gas present in the gas containing liquid stream;

(Q) recovering from the gas recovery zone of step (P) (i) a substantially methanol free recovered gas stream containing light byproducts and (ii) a degassed second crude liquid methanol stream;

(R) subjecting at least one stream selected from the hydrogen enriched gas stream of step (O) and the recovered gas stream of step (Q) to multistage compression in a multistage gas compression zone comprising a plurality of gas compression stages with an interstate cooler between the or each successive pair of gas compression stages;

(S) recovering from the multistage gas compression zone (i) at least one liquid condensate and (ii) a compressed recovered gas stream; and (T) passing the recovered compressed gas stream of step (S) to the second methanol synthesis zone.

2. A process according to claim 1, in which the carbonaceous feedstock comprises natural gas and in which conversion of the carbonaceous feedstock to synthesis gas is effected by a process selected from steam reforming, partial oxidation, and a combination thereof.

3. A process according to claim 1, in which partial oxidation is used in step (A) for the production of the synthesis gas and in which the synthesis gas is produced in step (A) at an elevated synthesis gas production pressure which is used as the compressed synthesis gas of step (B) without further compression.

4. A process according to claim 1, in which the pressure at which synthesis gas is produced in step (A) is compressed in step (B) to form the compressed synthesis gas by means of a synthesis gas compressor.

5. A process according to claim 4, in which compressor seal gases from the synthesis gas compressor of step (B) are supplied to the multistage gas compression zone.

6. A process according to claim 1, in which material of the hydrogen depleted gas stream of step (O) is used as fuel gas in the synthesis gas production plant.

7. A process according to claim 1, in which material of the hydrogen depleted gas stream of step (O) is used as supplementary feedstock in the first methanol synthesis zone.

8. A process according to claim 1, in which at least one stream selected from the secondary methanol stream of step (I) and the methanol-containing vent gas stream of step (I) is also supplied to the gas recovery zone of step (P).

9. A process according claim 1, in which the gas recovery step (P) includes a water wash step to remove substantially all methanol from the recovered gas stream.

10. A process according to claim 1, in which the degassed second crude liquid methanol stream of step (Q) is subjected to refining in a second methanol refining zone to produce (i) a light byproduct containing purge stream, and (ii) a methanol rich stream.

11. A process according to claim 10, in which the methanol rich stream is passed to the first methanol refining zone of step (I).

12. A process according to claim 1, in which the fusel oil stream of step (I) is subjected to distillation in a fusel oil distillation zone to provide (i) an overhead stream comprising methanol, (ii) a heavy byproduct purge stream, and (iii) a bottom fraction stream comprising water, and in which at least one stream selected from the overhead stream and the bottom fraction stream is passed to the first methanol refining zone.

13. A process according to claim 12, in which at least one stream selected from the heavy byproduct purge stream and the bottom fraction stream comprising water is used as feedstock or fuel in the synthesis gas production plant.

14. A process according to claim 1, in which the fusel oil stream of step (I) is subjected to distillation in a fusel oil distillation zone to provide (i) an overhead stream comprising methanol, and (ii) a bottom purge fraction comprising heavy byproducts and water, and in which the overhead stream is passed to the first methanol refining zone.

15. A process according to claim 14, in which the bottom purge fraction is used as supplementary feedstock or fuel in the synthesis gas production plant.

16. A process according to claim 1, in which compressor seal gases from at least one of the first and second gas recycle compressors are supplied to the multistage gas compression zone.

* * * * *